(12) United States Patent
Rigolone et al.

(10) Patent No.: US 7,958,805 B2
(45) Date of Patent: Jun. 14, 2011

(54) THREADING DEVICE ON A NUMERICALLY CONTROLLED LATHE

(75) Inventors: Franco Rigolone, Ponteranica (IT); Renato Rota, Carvico (IT); Oscar Gervasoni, Bergamo (IT)

(73) Assignee: Gildemeister Italiana S.p.A., Brembate Sopra (IT)

( * ) Notice: Subject to any disclaimer, the term of this patent is extended or adjusted under 35 U.S.C. 154(b) by 421 days.

(21) Appl. No.: 12/148,839

(22) Filed: Apr. 23, 2008

(65) Prior Publication Data
US 2008/0264220 A1  Oct. 30, 2008

(30) Foreign Application Priority Data

Apr. 26, 2007 (IT) .............. MI2007A0860

(51) Int. Cl.
*B23B 25/00* (2006.01)
*B23B 5/46* (2006.01)

(52) U.S. Cl. .................... 82/117; 82/DIG. 900

(58) Field of Classification Search ............ 82/117–124, 82/110, 50; 409/65, 76; 29/898.02
See application file for complete search history.

(56) References Cited

U.S. PATENT DOCUMENTS

| | | | | |
|---|---|---|---|---|
| 2,036,821 A * | 4/1936 | Munson | ............ | 82/119 |
| 2,934,689 A * | 4/1960 | D Amico | ............ | 318/629 |
| 3,129,592 A * | 4/1964 | Bracutt | ............ | 73/490 |
| 5,664,470 A * | 9/1997 | Garnett et al. | ............ | 82/121 |
| 5,813,806 A * | 9/1998 | Muller | ............ | 409/11 |
| 6,279,438 B1 * | 8/2001 | Delacou | ............ | 82/121 |
| 6,722,005 B2 * | 4/2004 | Sauter et al. | ............ | 29/40 |
| 2004/0231473 A1 * | 11/2004 | Geibler et al. | ............ | 82/124 |

* cited by examiner

*Primary Examiner* — Will Fridie, Jr.
(74) *Attorney, Agent, or Firm* — Kirschstein, et al.

(57) ABSTRACT

A piece-threading device on a numerically controlled lathe comprises a supporting assembly having an inner rotatively driven body which, on a side thereof facing a workpiece to be threaded, comprises a plurality of threading tools, the rotatively driven body having a built-in electrical rotor (9) to which an electric stator (8) also built-in in the supporting assembly is operatively coupled, the stator (8) having a plurality of circumferential channels (6) for circulating therethrough a refrigerating and lubricating fluid.

9 Claims, 3 Drawing Sheets

THREADING DEVICE ON A NUMERICALLY CONTROLLED LATHE

BACKGROUND OF THE INVENTION

The present invention relates to a piece-threading device to be used on a numerically controlled lathe.

As is known, in the medical field are conventionally used screws, stems or other mechanical pieces to be screwed into the bone structure of a patient.

At present, the best method used in the prior art for making threaded elements to be used in the medical or dental field, is a specifically designed cutting process, the so-called "swivel" threading process or, in a word-wide manner, the "Thread Whirling Process".

Prior methods allow to make threaded pieces with a variable pitch thread, a very long pitch thread, highly buttressed threads, bevel threads or variably buttressed threads.

It should be apparent that the selection of the thread will depend on the specific bone structure, the screw must be screwed into.

The prior machining method allowing to make different types of threads on a lathe, also allows to machine, without any technical problems, very hard metals, such as stainless steel, titanium or the like.

From the prior art it is also known that the surface quality of a thread depends on clearances which are present in the kinematic chain driving the tools used for performing the above mentioned thread whirling process.

The prior method for making the above mentioned threads, however, is not a continuous cutting method, but an interrupted cutting operation, like a milling machining operation, and this type of machining greatly stresses the driving means; moreover, because of unavoidable clearances, the surfaces of the resulting threads are inevitably affected by machining defects and rags.

Usually, in prior devices, the threading tools are driven by a driving motor through a series of gears which, because of their nature, necessarily require a minimum clearance, to provide a proper mutual meshing, and this clearance, even if it has a minimum value, negatively affects the precision and quality of the resulting thread surface.

To further limit the above undesired clearance, prior deriving gears have been recently replaced by a belt transmission, designed to allow the motor to rotatively drive the machining tool.

This approach, however, has the drawback that a resilient element in the form of a belt must be used in order to transmit the rotary motion from the driving motor to the machining tool. The use of a belt generates inevitable undesired oscillations in the rotary movement of the tool that must be subjected to continuous control. Moreover, the driving belt must be subjected to periodic controls for its inevitable wear and to repeatedly accomplish the tensioning thereof.

Thus, both the above mentioned gear assembly and driving belt, as conventionally used for rotatively driving prior threading tools, cause an undesired increase of the overall size of the device.

Moreover, it has been also found that in prior threading device, also called "turbothreaders" designed for making a swivel thread, it would be absolutely necessary to rotatively drive the head/spindle assembly for performing the thread helix; moreover, for making some types of threads, it would be indispensable to tilt the threading head with respect to the horizontal plane and, moreover, to provide a tool holder spindle having a conical inner configuration, in order not to impact against the workpiece during the threading operations.

SUMMARY OF THE INVENTION

Accordingly, the aim of the present invention is to overcome the above mentioned drawbacks of the prior art, and improve the cutting threading method so as to provide variable pitch threads free of metal rags and with thread surfaces having a minimum roughness, while allowing to omit prior gear cascade arrangements or belt drives to rotatively operate the threading tool.

According to the present invention, the above mentioned objects are achieved by a threading device for threading pieces designed to be used in the medical field, said device comprising a supporting assembly having an inner rotatively driven body, which, on a side thereof facing the workpiece to be threaded, comprises a plurality of threading tools, said rotatively driven body housing an electric rotor to which an electric stator built-in in said supporting assembly is operatively coupled.

Advantageously, said stator has a stator outer circumference including a plurality of channels for circulating therethrough a refrigerating fluid.

Moreover, the electric stator is encompassed by a sleeve having a plurality of circumferential channels, therethrough a refrigerating and lubricating fluid flows. Said refrigerating and lubricating fluid passes through the inside of the supporting assembly and exit the latter through an opening.

Advantageously, the related interface includes electric cables to power supply the electric motor and the ducts required for pressurizing the device.

Between the device and the machine tool a single interface is provided.

Advantageously, a speed sensor for controlling the electric motor, and being coupled to the rotary body is further provided.

The electric motor driving the rotary body may be advantageously controlled by control means of a MRAS type (Model Reference Adaptive System), thereby allowing the speed or revolution sensor to be omitted.

Further characteristics of the invention will become apparent from the sub-claims and the accompanying disclosure and drawings.

BRIEF DESCRIPTION OF THE DRAWINGS

The subject matter according to the present invention will be disclosed and illustrated in a more detailed manner hereinafter, with reference to a preferred embodiment given only by way of an example. In the drawings.

DESCRIPTION OF THE PREFERRED EMBODIMENT

Figure 1:
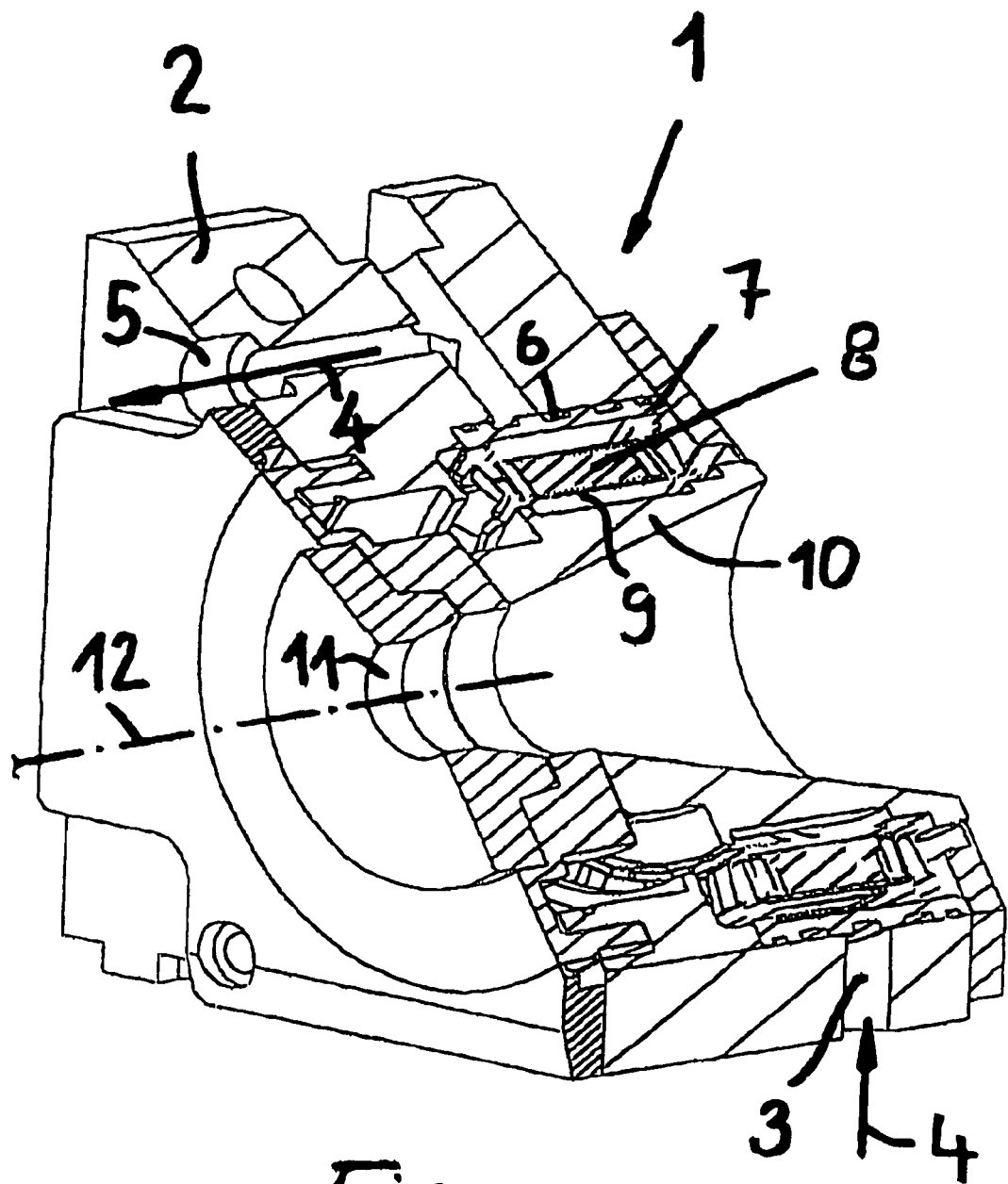
FIG. 1 is a schematic partially cross-sectioned view of the novel threading head including a novel driving motor.

As shown in FIG. 1, the threading device according to the present invention, which has been generally indicated by the reference number 1, comprises a supporting assembly or body 2, having a throughgoing opening 3 for supplying a refrigerating and lubricating fluid 4.

The supporting body or assembly 2 is mounted on a slide of a machine tool, not herein shown.

The refrigerating and lubricating fluid passes through channels, not specifically shown, of the supporting assembly 2, as it will be disclosed in a more detailed manner hereinafter, said fluid 4 exiting the supporting assembly 2 through an outlet channel 5.

Figure 2:
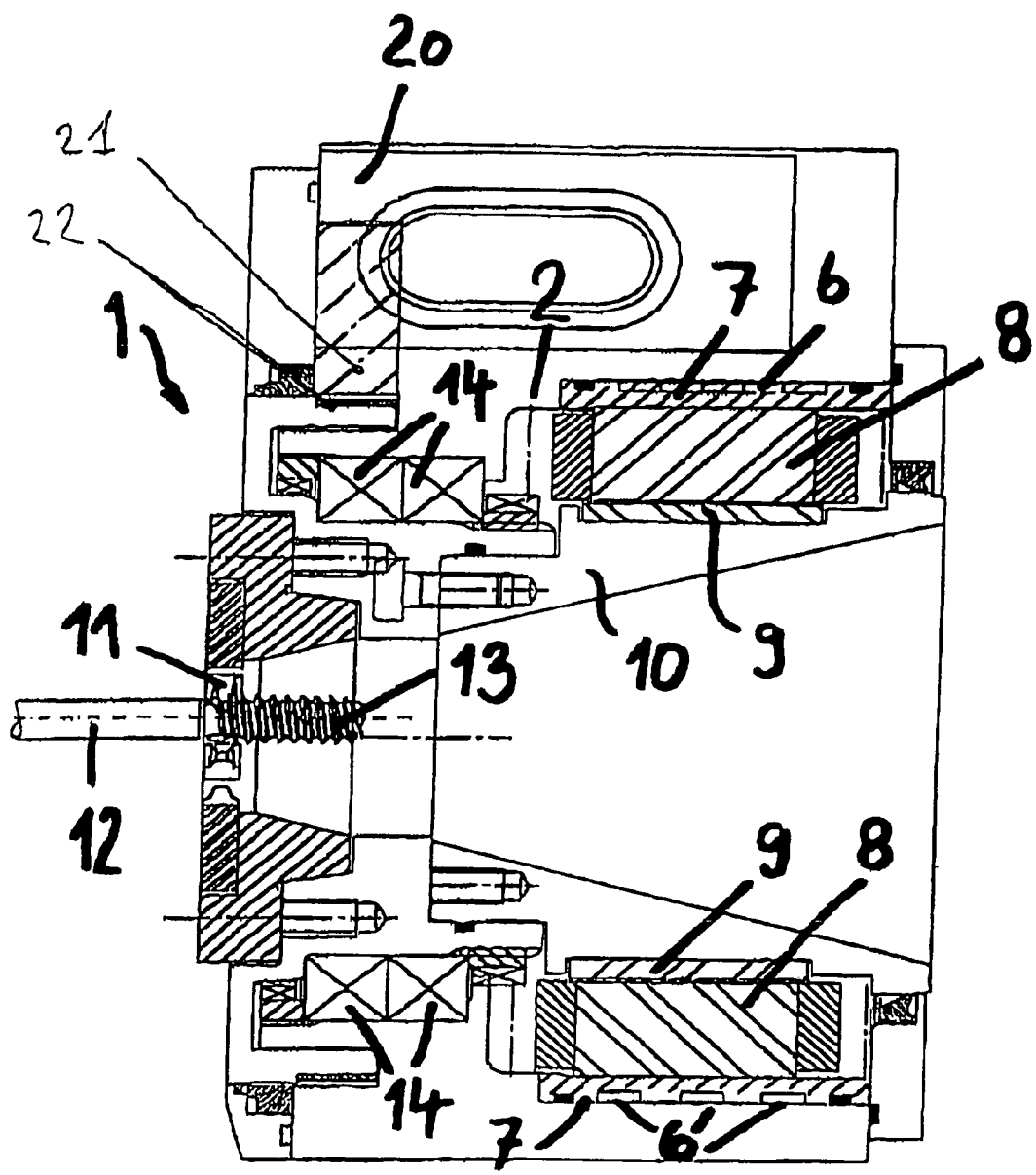
FIG. 2 is a cross-sectional view of the threading head.

Before exiting said supporting assembly or body 2, the refrigerating fluid 4 passes through a plurality of circumferential channels 6 of an annular body 7 encompassing the stator 8 operating in cooperation with a rotor 9 integral with a further body 10 which, at a region 11 thereof, supports a plurality of machining tools (not shown in FIG. 1) for machining a bar, schematically indicated by 12. FIG. 2, is a cross-sectional view showing the body 10 of the device 1, integral with said electric rotor 9, which is rotatively driven through said electric stator 8, said electric rotor 9 and stator 8 forming together an electric motor.

To said electric stator 8 is operatively coupled said tubular sleeve body 7, including said plurality of circumferential channels 6, to which refrigerating fluid for removing the generated heat is supplied.

FIG. 2 shows moreover in a very clear manner the arrangement of the threading tools 11 for threading, as desired, the free end portion of the bar 12.

The refrigerating fluid 4, exiting the opening or outlet 5 of the supporting assembly 2, as is shown in FIG. 1, is not only used as a refrigerating fluid proper passing through the channels 6 of the annular body 7; in fact said refrigerating fluid 4, upon exiting the supporting assembly 2 through the channel 5, will moreover freely descend, to be also used as a refrigerating fluid for the machining tools 11 forming threads 13 on the free end portion of the bar 12 which threaded bar will be finally cut to any desired length.

After the threading operation, the fluid 4 will be filtered and fed again to the cooling channels 6.

As is further shown in FIG. 2, the rotary body 10 is very accurately supported on said supporting assembly 2 by precision bearings 14.

Thus, the provision of said precision bearings 14 as well as of the electric rotor 9 in a single body with the rotary body 10 and a toroidal stator 8 fixedly mounted within the supporting assembly 2, and of the cooling channels 6 encompassing the stator 8 body, allows the machining tools 11 to be directly driven with a very high precision, without using, as in the prior art, a composite driving assembly including a series of gears, a trapezoidal drive belt or the like.

Moreover, the device 1 comprises an interface 20 to properly drive and control the motor 8, 9, which interface 20 is advantageously operatively coupled to a machine Numeric Control Device (not shown).

Said interface, moreover, is so pressurized as to prevent machining chips from depositing in the apparatus and wearing rotary parts of the latter.

Thus, said single interface providing both a passage for the electric motor power supply cables and a pressurized operating environment, allows to make a compact and operatively flexible device, which can be easily and quickly supported by a slide of any desired single or multiple spindle machine tool without the need of modifying the latter.

Figure 3:
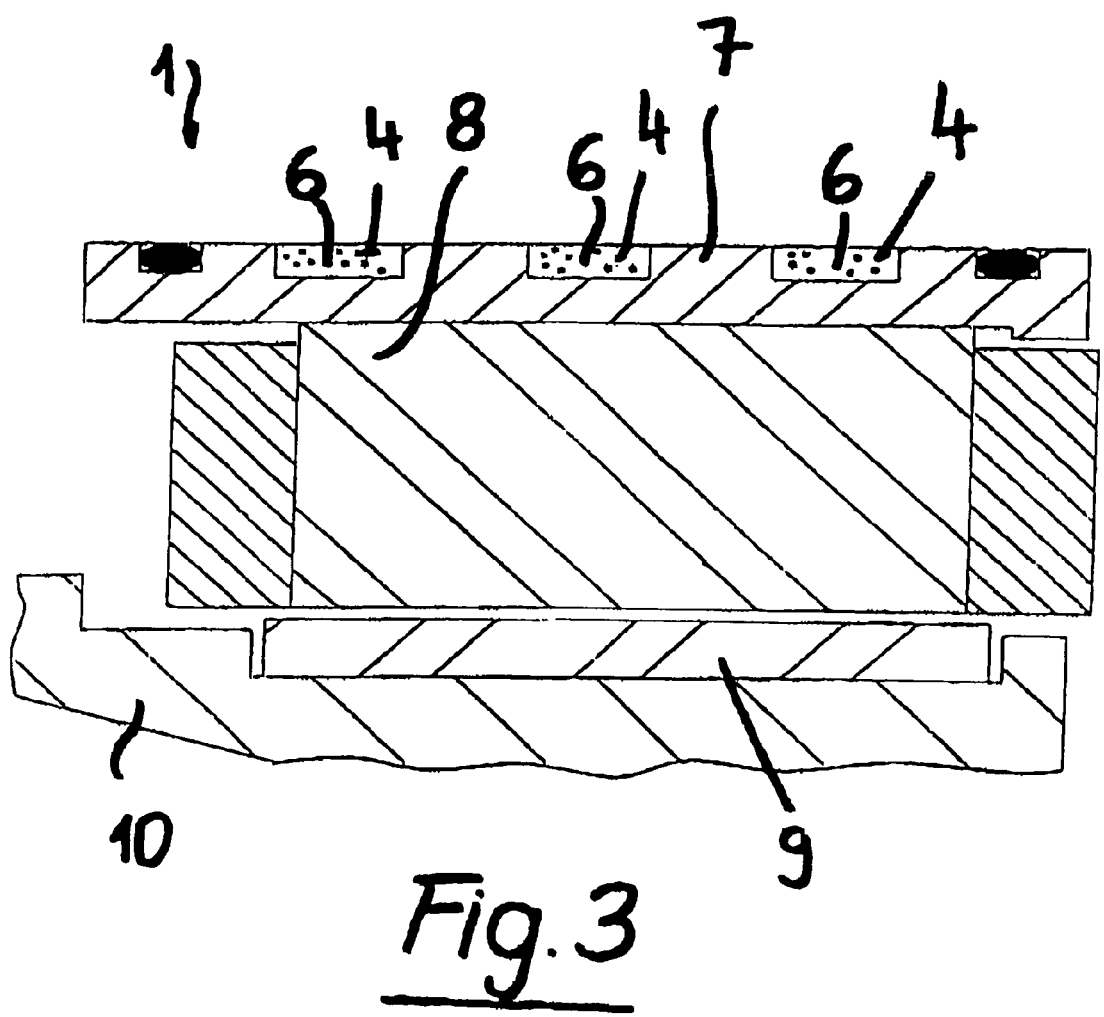
FIG. 3 is a further schematic partial cross-sectioned view showing a portion of the threading head with the driving motor stator and rotor coupled to the rotary driving assembly of the threading device.

FIG. 3 shows a schematic cross-sectional view of the portion 10 of the supporting assembly 2, said portion 10 supporting not shown threading tools and comprising said electric rotor 9 forming, with said electric stator 8, a synchronous brushless electric motor 8, 9 (for example of a type offered and produced by the Company Phase Motion Control of Genoa). FIG. 3 also clearly shows the circumferential channels 6 formed in the sleeve 7 therethrough said refrigerating fluid 4 supplied, for example, through a channel 3 of a central unit (not shown) flows, said fluid 4 being so temperature controlled as to properly cool said stator 8; moreover said fluid upon exiting the device 1 through the channel 5 (FIG. 1) will be also conveyed to the machining tools 11 to also properly lubricate and cool the latter, and remove any machining chips from the resulting thread 13 at the free end portion of the bar 12.

In FIG. 2, the reference number 21 shows the fixed portion and the reference number 22 the rotary portion of a speed sensor for sensing the rotary speed of the body 10.

According to a modified embodiment of the invention, to further improve the compactness and operating flexibility of the apparatus, it would be also possible to omit the speed sensor, and detect said rotary speed by reading out the operating current of the motor thereby properly controlling said motor by a sensorless arrangement, as controlled by a MRAS or Model Reference Adaptive System.

Thus a turbothreading device of very simple and compact construction will be obtained.

The invention claimed is:

1. A device for exteriorly threading a rod-shaped workpiece in a machine tool, comprising:
   an annular hollow sleeve extending along a longitudinal axis and formed with a plurality of circumferential channels;
   a support for supporting the annular sleeve, the support having an inlet for admitting a cooling lubricating fluid into the channels, and an outlet for discharging the cooling lubricating fluid from the channels;
   an electric motor built into the support for rotating a thread-cutting tool about the longitudinal axis to exteriorly thread the workpiece, the motor having a stator supported and surrounded by the annular sleeve and cooled by the cooling lubricating fluid in the channels during rotation of the thread-cutting tool, and a rotor surrounded by the stator; and
   a tool holder for holding the thread-cutting tool concentric with the longitudinal axis, the tool holder being coupled to the rotor for joint rotation about the longitudinal axis.

2. The device according to claim 1, wherein the inlet extends radially of the longitudinal axis, and wherein the outlet extends parallel to the longitudinal axis.

3. The device according to claim 1, wherein the support has an axial end face, wherein the tool holder holds the thread-cutting tool in a plane perpendicular to the longitudinal axis adjacent the axial end face of the support, and wherein the outlet has a discharge opening adjacent the axial end face of the support and above the tool holder to enable the cooling lubricating fluid discharged from the discharge opening to flow onto the tool holder to thereby cool and lubricate the thread-cutting tool.

4. The device according to claim 1, and friction-reducing bearings between the support and the tool holder.

5. The device according to claim 1, wherein the tool holder is coupled to the rotor with a gear-free and a belt-free coupling.

6. The device according to claim 1, and a control interface on the support for controlling the motor.

7. The device according to claim 1, and a speed sensor coupled to the motor for sensing a rotary speed of the rotation of the tool holder.

8. The device according to claim 1, and a model reference adaptive system (MRAS) controller for determining a rotary speed of the rotation of the tool holder from an electrical operating current of the motor.

9. The device according to claim 1, wherein the device is mounted on a numerically controlled lathe for exteriorly threading the workpiece as one of a medical and a dental threaded element.

* * * * *